United States Patent [19]
Dechene et al.

[11] Patent Number: 5,049,819
[45] Date of Patent: Sep. 17, 1991

[54] MAGNETIC RESONANCE ANALYSIS IN REAL TIME, INDUSTRIAL USAGE MODE

[75] Inventors: Ronald L. Dechene, Boxford, Mass.; Thomas B. Smith, Atkinson, N.H.; Ajoy Roy, Danvers, Mass.

[73] Assignee: Auburn International, Inc., Danvers, Mass.

[21] Appl. No.: 573,639

[22] Filed: Aug. 27, 1990

Related U.S. Application Data

[63] Continuation-in-part of Ser. No. 374,493, Jun. 30, 1989, Pat. No. 5,015,954.

[51] Int. Cl.$^5$ ............................................. G01R 33/20
[52] U.S. Cl. ................................................... 324/307
[58] Field of Search ............... 324/300, 307, 309, 310, 324/311, 312, 313, 314, 318, 322; 128/653 A

[56] References Cited

U.S. PATENT DOCUMENTS

4,719,582 1/1988 Ishida .................................. 324/312

Primary Examiner—Michael J. Tokar
Attorney, Agent, or Firm—Jerry Cohen

[57] ABSTRACT

Pulsed NMR system for industrial purposes comprising sample throughput system (P, LI, V1, V2) magnetic field adjustment (120, 124) and thermal adjustment (134–138 and 142–146). The resonance is established by a coil (100), excited by a transceiver (104) and interacting with the sample and the magnetic field at resonance to establish received and digitized free induction decay curve forms (C) which are automatically analyzed into Gaussian and exponential components—providing simplified high speed computation means with repetitive test sequence and thermal controls that systematically minimize errors to assure reliable determination of target nuclei quantities in successive samples from an industrial process and utilizing Hahn spin echo based equipment to automatically adjust the analysis of one or more of the analyzed components.

8 Claims, 5 Drawing Sheets

Regression: 0.94873
Correlation: 0.99

UNSCRAMBLER general plot    June 18 1990    8.24

MAGNETIC RESONANCE ANALYSIS IN REAL TIME, INDUSTRIAL USAGE MODE

CROSS REFERENCE TO RELATED APPLICATIONS

This application is a continuation-in-part of the Dechene et al. copending application, Ser. No. 374,493, filed June 30, 1989, and now Pat. No. 5,015,954. The disclosure of said application is incorporated herein by reference, as though set out at length herein.

FIELD OF THE INVENTION

The present invention relates to an instrument for measurement of the type and quantity of lattice bound and free magnetically active nuclei within successive samples of a process material flow through pulsed nuclear magnetic resonance (NMR) techniques and more particularly the application of such measurement to industrial process control of moisture content, polymer content, crystallinity fraction, and other percentages of components analysis and other parameters.

BACKGROUND OF THE INVENTION

Pulsed NMR spectroscopy is described in our above-cited U.S. application Ser. No. 374,493. This technique uses a burst or pulse which is designed to excite all the nuclei of a particular nuclear species of a sample being measured (the protons, or the like, of such sample having first been precessed in an essentially static magnetic field); in other words the precession is modified by the pulse. After the application of the pulse there occurs a free induction decay (FID) of the magnetization associated with the excited nuclei. Traditional Fourier Transform analysis generates a frequency domain spectrum which can be used to advantage in studying the nuclei of interest. The duration of the pulses, the time between the pulses, the pulse phase angle and the composition of the sample are parameters which affect the sensitivity of this technique. These frequency domain techniques are not easily useable in industrial applications, especially on-line applications.

Application Ser. No. 374,493 showed an improved NMR measurement system which leads to accurate, fast determination of the types and quantity of the nuclear species of interest, the use of time domain analysis in such a system, its application to the industrial, on-line problems of monitoring and controlling processes, measuring free and bound water in organic or inorganic substances (based on hydrogen nuclei modified-precession analysis) and other parameter measurement (based on hydrogen or other sensitive species including e.g., sodium-23 or carbon-13), accommodating the dynamics of industrial on-line applications including variations of density, temperature, packing and size factors, friction and static electricity, vibration and frequent, repetitive, cyclic and non-cyclic measurements, and using such magnetic resonance techniques in polymer analysis, including density, all with enhanced accuracy and reliability of data obtained and while achieving the necessary practical economies.

The object of the present invention is to extend those achievements further in relation to industrial on-line processing, and the like, as applied to mixed species (or mixed phases) of NMR-active materials and more particularly foodstuffs and plastics materials (and being applicable to many other NMR-active materials) with a third component such as oils/fats or solvents in addition to two main components (moisture/solids, crystalline/amorphous).

SUMMARY OF THE INVENTION

The objects are met by a pulsed NMR system effecting a reliable extraction of free induction decay data in a way that is practical in an industrial on-line context and economically practical. The system is characterized by provision of a base magnetic field homogeneity to a reasonable degree and offset of inhomogeneity effects, temperature stabilization to a reasonable degree and offsets of thermal drift effects and use of multiple runs (50-500) for each measurement with digital data reduction and use of statistical methods or other data manipulation for industrially effective measurement. These data can be represented, for discussion/analysis, as a free induction decay curve (FID) with attention to time sequence components of a first, very fast, essentially Gaussian portion followed by a slower, essentially exponential region representative of proton relaxation after an initial excitation by a pulse of transmitted and resonantly coupled radio frequency energy that induces a modification of the precession of protons in the sample being measured in a high static magnetic field.

The Gaussian FID portion is based on measurement data points of magnetization decay of immobile or highly constrained protons present in the sample and picked up at the NMR system's receiver; this portion is usually based on the response of bound proton species such as the hydrogen or hydrate content of chemical compounds (or similarly for many other NMR-active species, e.g., sodium-23 or carbon-13, which are chemically bonded). The exponential FID portion is usually based on loosely constrained or unconstrained NMR-active species such as moisture physically present in a sample but essentially chemically unbonded thereto. The Gaussian and exponential FID portions and the FID as a whole can be extrapolated to a decay origin usually set at the time center of the excitation pulse. Zero time intercepts of these curves (i.e., FID and one or more of its component curve portions) provide ratio data using the FID intercept and/or intercepts of one or more of the curve portions to determine e.g. free vs. bound water in a moist material (e.g. for process control of industrial chemicals, minerals and metals, agricultural commodities, processed foods by determining moisture content for upstream or downstream correction or for acceptance/rejection purposes). Instead of determining moisture in, say a food product the object may be to determine ratio of relatively crystalline and non-crystalline components of a material, e.g. hard and soft components of a plastic material and that is accomplished in a fashion analogous to the moisture measurement. Density can also be determined through the invention because the FID varies predictably as a function of density.

Within a given such measurement, a source of error can arise if the material has a fat or oil or organic solvents component that has an exponential response similar to that of moisture content or the like. Such fats or oils or solvents may appear in foods. In some instances, it may be desirable to actually determine such fat, oil or solvent content—not merely separate it out from determination of moisture or the like. Similarly, residual solvents may appear in plastics or other industrial materials as an error factor to be resolved and/or as a target parameter to be measured. The NMR response of such solvent or fat/oil portion can be isolated by use of Hahn spin echo technique as an extension of each of several measurement cycles. When a FID has progressed from initial excitation and Gaussian and exponential response portions, a new secondary refocussing pulse (usually a 180° or pi rotation compared to the initial excitation 90° or pi/2 pulse) is applied to produce an echo and then a third pulse (also pi) is applied to obtain a second echo which is reflective entirely of the solvent or oil/fat content. That second echo can be treated independently of stored data of the first FID and then substrated from the first FID to provide a valid first FID intercept (exclusive of oil/fat effects) which is reduceable via ratio analysis with that FID's Gaussian portion intercept to derive valid solids/liquid content (or crystallinity, or moisture) data.

The invention also comprises the direct extraction of data, with appropriate calibration, from the tertiary FID to show the solvent or fat/oil content. Such technique can be extended, to some degree, to distinguish among sub-components of such solvents or fats/oils.

The measuring system of the invention comprises economically scaled down and industrially hardened portions, relative to the widely used laboratory systems. A magnetic essentially fixed field comprises closely spaced pole pieces with a 4,000–8,000 Gauss field (about 4,700 Gauss, nominally). Helmholtz coils are provided which are adjustable to provide rapid adjustments for the precise, correct field and overlaid with coarse, slower adjustments to thermal environment. This is to assure that the product of a materials related constant (gamma) multiplied by the magnetic field strength, which is resonant frequency, will match excitation frequency. Still further fine adjustment is made in signal processing as described below.

As in the system of Ser. No. 374,493, the present invention accommodates great streams of data in practical ways through features, described below, which are inter-related to the thermal controls to provide a measuring system meeting the foregoing objects. The materials of construction are also integrated into the reliability considerations, as described below. Measurement of a sample is often accomplished in less than a few minutes (in contrast to hours-long measurements of many prior art systems).

The measurements made through the present invention based on ratios of intercepts and/or integrated areas under curves and/or peak analysis are independent of weight or volume of sample in a measuring region whereas precise weight measurement is a necessary feature—and limitation of—many prior art systems.

Prior art efforts at industrial on-line measurement of the same parameters as are treated herein have involved non-NMR gravimetric, radioactive, acoustic, optical and electrostatic/capacitive systems, none wholly satisfactory for present purpose and NMR usage in support of continuous industrial processes has been a forcing of off-line laboratory instruments into service [at great expense and nevertheless with inadequate sampling] or some early efforts of the 1980's at industrial hardened pulsed NMR instruments making use of only one or two data points for FID analysis. The present invention together with the invention of said Ser. No. 374,493 breaks out of all those dead ends.

Laboratory methods of frequency domain NMR analysis are described for crystallinity content determination in, e.g., Spiess, "Molecular Dynamics of Solid Polymers As Revealed By Deuteron NMR", 261 Colloid & Polymer Science 193–209 (1983) and Kauffman et al., "Determination of Transition Temperatures and Crystalline Content of Linear High Molecular-Weight Polyethylene by Proton NMR Spectroscopy", 27 Jl. of Polymer Science 2203–2209 (1989). Time domain analysis using pulsed and multiple pulsed NMR/free induction decay in coals for detection of free radicals therein is shown in the laboratory systems of Gerstein et al. (Iowa State University Ames Laboratory) reported in "Utility of Pulse Nuclear Magnetic Resonance In Studying Protons In Coals", 81 Jl. of Phys. Chem. 566–571 (1977) and "1H Nuclear Magnetic Resonance Studies of Domain Structures In Polymers", 52(9) J. Appl. Phys. 5517–5528 (1981). The instruments or former instruments of IBM Federal Systems Division model and Brucker GmbH model P201 and the description in U.S. Pat. No. 4,430,719, granted Feb. 7, 1984, to Pearson are the earlier attempts referred to above at industrial use of NMR methods. The Pearson work was embodied in 1985 industrial plant control work of Kaiser Aluminum & Chemical Corp. It was not effective as a reliable quantitative device. Auburn International, Inc. offered the Pearson/Kaiser product for sale in 1987–1988 and it could not meet the needs of industrial on-line monitoring. These failures were followed by the making of the invention of Ser. No. 374,493 and the latter as enhanced through the present invention, both solving the industrial on-line problem for various materials.

Other objects, features, and advantages will be apparent from the following detailed description of preferred embodiments taken in conjunction with the accompanying drawing(s) in which:

DETAILED DESCRIPTION OF PREFERRED EMBODIMENTS

Figures 1, 2:
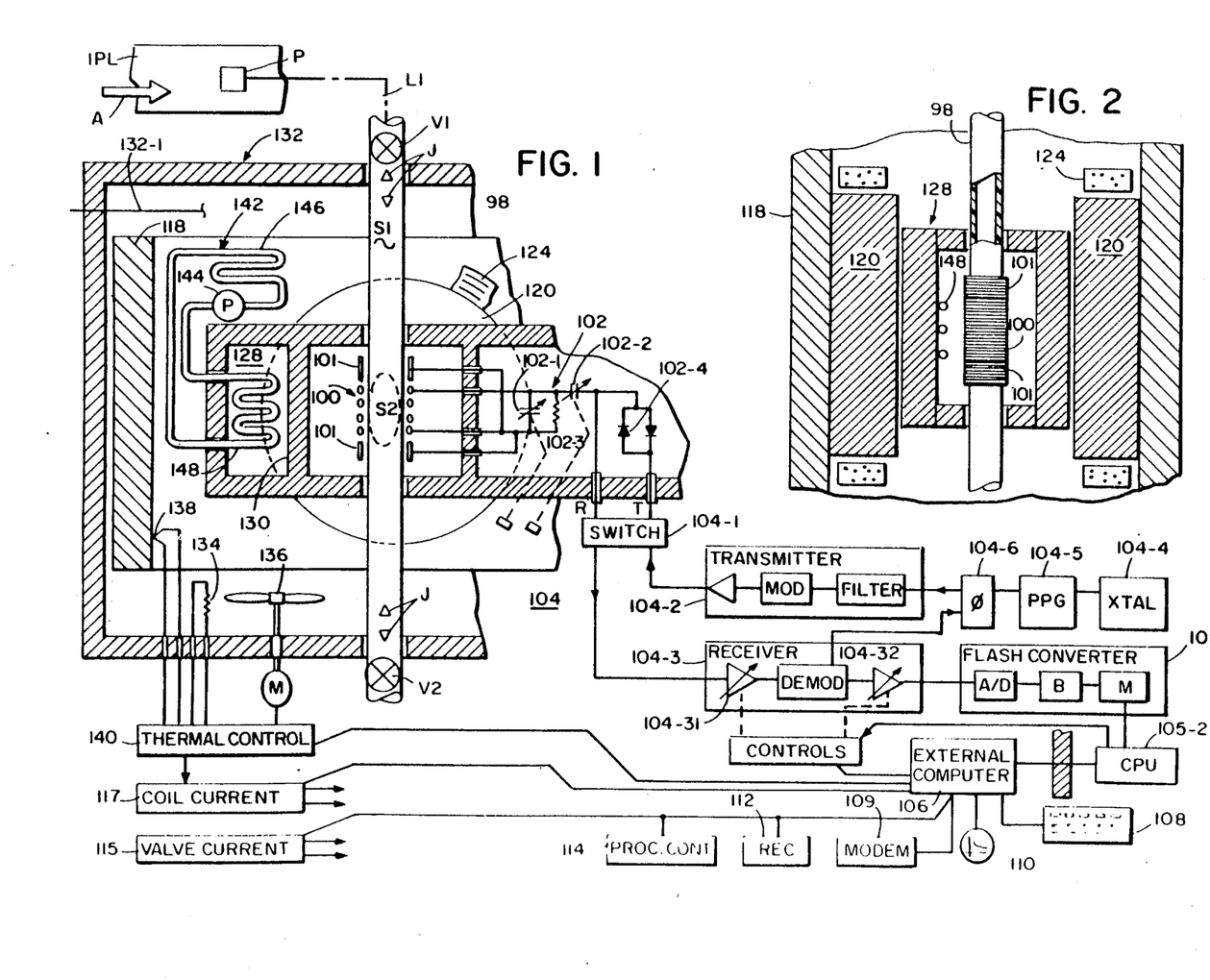
FIGS. 1 and 2 are lateral and cross-sections of a preferred embodiment of the invention including electrical block diagram components.

FIGS. 1-2 show transverse and cross sections with block diagram inserts of a first embodiment of the apparatus and method of the invention. An industrial process line IPL has material flowing as indicated by arrow A. Some of the material is captured by a probe P and fed through an inlet line LI to a sample region S1. The said region is defined by a tube 98 typically a foot long made of an essentially non-magnetic, nonconducting material which does not itself generate substantially interfering FID signals (glass, certain ceramics, certain plastics or hybrids). The sample region is defined between inlet and outlet valves V1 and V2. Gas jets J are also provided. These are pulsed on/off repeatedly to agitate fluent sample materials during sample admission and expulsion. The region S2 is the critical portion of the sample. It is surrounded by a sample coil 100 tuned to resonance and driven by a tuning circuit 102 and related transmitter/receiver controller 104. Grounded loops 101 are Lenz Law shields which are provided above and below coil 100 to help shape the field of coil 100—i.e., contain the field established by an excitation pulse. The controller 104 includes an on-board microprocessor and required power supply elements, memory, program and I/O decoding suitable to interconnect to the hardware shown and to an external microcomputer 106 with keyboard 108, monitor (or other display) 110, recorder 112 and/or process controller 114 (to control the process at IPL). The operator initiates and controls operation from the display keyboard 108 and the resulting data and signals are subsequently shown on the display 100 and utilized in 110, 112 and/or 114. The computer 106 also controls instrument operation conditions.

The region S2 of tube 98 and coil 100 are in a static, but adjustable, crossing magnetic field defined by a magnetic assembly 116 which comprises a yoke 118, pole pieces 120, surrounding Helmholtz coils 124, and a coil current generator 117. The critical sample region S2 of the tube 98 and magnet are contained in a metallic (but non-ferromagnetic) box 126 with highly thermally conductive face-plates 128 and internal partitions 130 and over-all mass related to each other to minimize harmonics and other interferences with a signal emitted from coil 100 to a sample and/or returned from the sample for pick-up by coil 100 and its tuned circuit 102 and transmit/receive controller 104.

The magnetic assembly 116 including yoke 118, and other parts therein as shown on FIGS. 1-2, is in turn contained in an environmental control chamber 132 with gas fill and purge controls (not shown), an internal gas heater 134, a motor M driving fan 136, and a temperature sensor 138 which can be applied to the yoke or other detection region whose temperature is reflective of the temperature at pole pieces 120 and in the sample region therebetween. A thermal controller 140 processes temperature signals from 138 to adjust heating-/circulation at 134/136 as a coarse control and to adjust current through the Helmholtz coils 124 at magnet pole pieces 120 as a sensitive and fast fine control, as well as implementing general control instructions of computer 106. Further thermal stabilization may be provided by a closed loop heat exchanger 142 having pump 144 and coils 146 attached to yoke 118 and coils 148 attached to the plates 128 of box 126.

The strength, consistency and constancy of the magnetic field between poles 120 in the region S2 of the sample is thus controlled by a uniform base magnetic field in the entire region S2. The Helmholtz coils 124 are energized by the coil current controller 117 to accurately trim the final magnitude of the field in which the sample is placed. This field is the vector addition of the fields due to the magnet poles 120 and the Helmholtz coils 124. The controller 117 sets the current through the Helmholtz coils 124 using current generators. The coils 124 are wound around the magnet pole pieces such that the magnetic field created by the current in the coils 114 can add to or subtract from the field created by the magnet pole pieces. The magnitude of the current through the coils 124 determines the strength of the field added to or subtracted from the field due to the magnet pole pieces (and related yoke structure) alone.

The actual determination of the current through the Helmholtz coils is accomplished by carrying out the magnetic energy and resonance techniques hereinafter described in preliminary runs and adjusting Helmholtz current until the maximum sensitive resonance is achieved.

The major elements of electrical controls are in tuner 102, including coils 100 and 101 and variable capacitors 102-1 and 102-2, resistor 102-3 and diodes 102-4 and constructed for tuning to Q of twenty to fifty to achieve coil 100 resonance, and control 104 including a transmit/receive switch 104-1, a transmitter 104-2 and receiver 104-3, a crystal oscillator 104-4, gated pulse generator (PPG) 104-5, and phase shifter 104-6. The crystal provides a nominal twenty Megahertz carrier which is phase modulated or demodulated by the MOD, DEMOD elements of transmitter 104-2 and receiver 104-3. The receiver includes variable gain amplifier elements 104-31 and 104-32 for operation. The analog signals received are fed to a high speed flash converter 105-1 and internal (to the instrument) CPU element 105-2, which provides data to an external computer 106 which has a keyboard 108, monitor 110, modem 109, recording elements 112 and process controller elements 114, e.g., for control of valves V1, V2 via valve controls 115 and/or to coil current controls 122, all via digital-analog converters (not shown).

Figure 3:
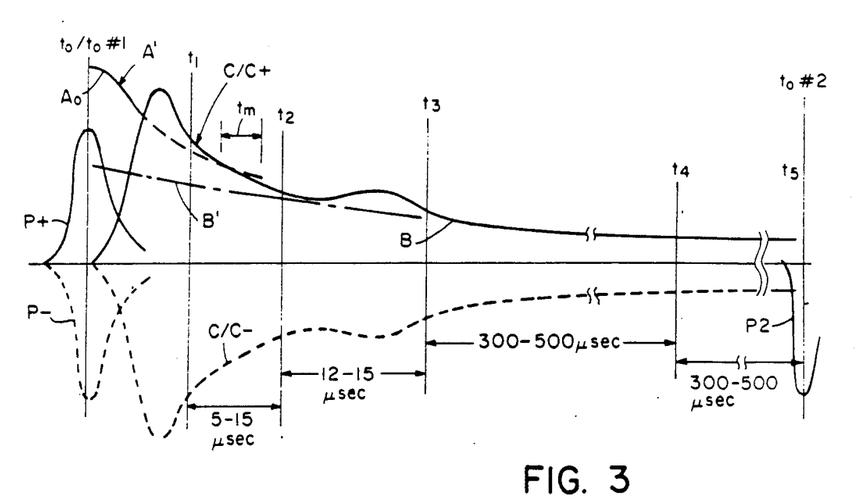
FIG. 3 shows the voltage-time waveforms of the free induction decay (FID) of the embodiment of FIGS. 1-2 in the course of operation.

The excitation of coil 100 and excitation-precession of the sample's proton content and subsequent relaxation/decay produces a received FM signal that, after demodulation, controlled gain amplification, A/D conversion and plotting of points has the free induction decay (FID) curve shape C shown in FIG. 3. FIG. 3, voltage-time trace, shows the elements of a "cycle" (with (+) and (−) sub-cycles) of excitation of a sample and free induction decay. In each (+)/(−) sub-cycle a pulse of excitation energy is applied. The excitation pulse center is taken as t0. The transceiver 104 electronic components do not receive effectively until saturation effects are overcome at t1. Then a useable curve C(+) or (C−) is developed. The signal processing equipment can add or subtract consecutive C+ and C− forms for useful adjustment as described below.

The FID curve data is stored in the external computer 106 where a program finds the best curve to fit each stored FID curve. The FID curve C has two component parts shown as A and B in FIG. 3. The A curve which dominates the first part of the FID curve is a Gaussian curve while the B curve which dominates that later part of the FID curve is an exponential decay. The Gaussian and exponential portions are respectively controlled by bound and unbound proton content of the samples (e.g., (1) water or hydration molecules and other water (moisture) content of the sample mass, (2) crystalline and amorphous contents where they both occur, including mixtures of highly and lightly polymerized materials and (3) components of a mixed elastomer-polymer). The determination of the type of curve which makes up the FID curve C is important because once the curves are known they can be extended back to a time origin (shown as t0-1, i.e., excitation of a Cycle 1), which is at the theoretical center of the transmitted burst signal. This is important since there are saturation effects of the instrument's electronic gear which occur during and after the burst signal to t1. During this time measurements cannot be accurately taken, yet the area of interest under the curve, which is a measure of the number of nuclei in the sample, extends from t0 to t4 beyond which the curve is too small to matter and the electronics need recovery time to prepare for the next cycle (beginning with a pulse centered at t02).

Each (sub) cycle goes on to t5 to allow for recovery i.e., essentially full relaxation of the protons of the sample—before beginning a new transmit signal burst (t0-2). Typically, an excitation pulse interval is five to ten microseconds, the t0—t1 time is five to fifteen microseconds (the shorter the better), t1-t2, where effects due to bound nuclei (Gaussian) are predominant is five to fifteen microseconds duration (with critical measurement taken at a narrower region tm); t2-t3 is an intermediate region of fifteen to twenty-five microseconds duration characterized by phase cancellation effects, t3-t4 is a region where the unbound (exponential) component predominates and it is three hundred to five hundred microseconds duration during that part of the decay. The closest exponential curve is fitted to the C curve in the t3-t4 region where the C and B curves are essentially equal and this B curve is extrapolated back to t0, i.e., establishing a curve B and its phantom B' component and B0 intercept at t0. This exponential curve is subtracted from the C curve in the area (t2-t3) where the A (Gaussian) curve is dominant. The resulting curve is then fitted with the best least squares Gaussian curve. This best Gaussian curve is then extrapolated back to t0 to establish A including its phantom A' component and A0 intercept at t0. There is a final t4-t5 region, for allowing recovery (re-equilibration) of the sample material, which can be on the order of hundreds of milliseconds up to several seconds.

The resulting data utilized in the computer 106 (FIGS. 1-2) is the A curve and the B curve and ultimately their intercepts at t0 and the B0/A0+B0 ratio thereof. Each of these curves (and their intercepts) has been experimentally and theoretically related to the same nuclei of interest, but with the group of the nuclei which yield the A curve (Gaussian) bound in a lattice structure. The nuclei which yield the B curve (exponential) are unbound.

The data can be used as a QC type measurement or as an online control parameter which is fed back to control a process, back in line IPL (FIG. 1) or related equipment (e.g., in drying or baking a food product, conducting a continuous chemical or metallurgical reaction process, etc.)

The form of the input operating parameters of the system can be wide reaching to include previously stored parameters in PROMs or ROMs or in magnetic storage media such as disks or tapes or inputs sent in over telephone line and modem 109. The generation of the excitation pulse can be accomplished with many techniques including a coil or antenna arrangement. The steady magnetic field can be generated by electromagnets, permanent magnets, electromagnetics with superconducting winding or other standard techniques of generating magnetic fields.

Figure 4:
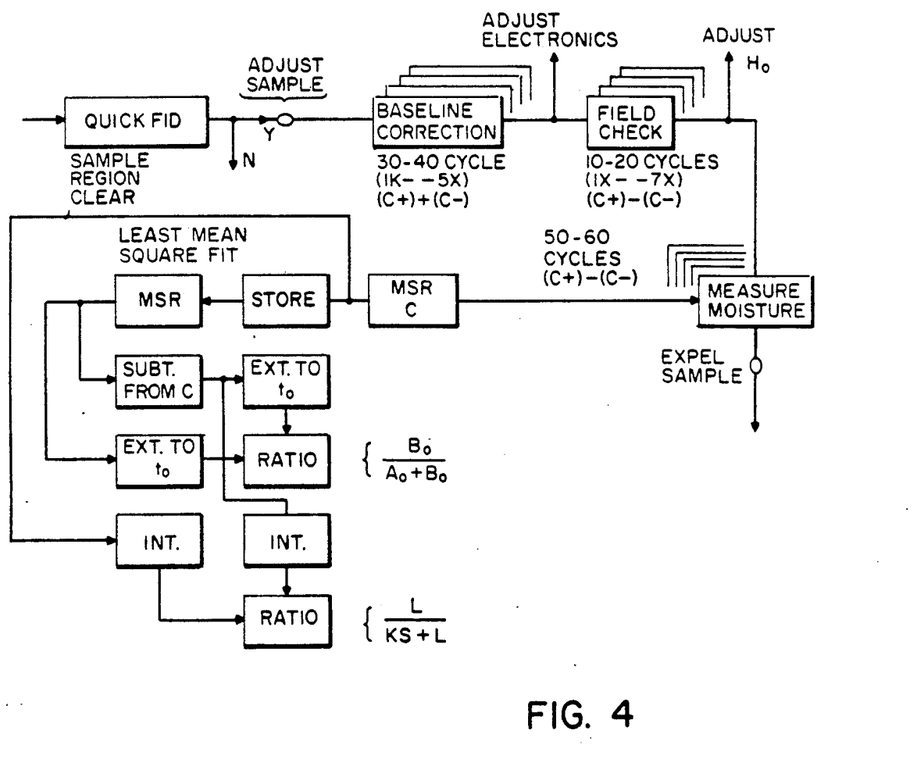
FIG. 4 is a flow chart of measuring steps utilizing the FIGS. 1-2 apparatus including its signal processing elements, (the activity of which is illustrated by the FIG. 3 waveforms).

FIG. 4 is an expanded flow chart showing the steps of measurement to establish effective industrial measurement. First a single free induction decay curve C is established to see if the sample area is clear (Quick FID) in an abbreviated cycle of attempting to establish a curve C. If the sample region is not clear (N), measurement is interrupted to allow valve V2 (re)opening and operation of jets J and gravity to clear the region. A new Quick FID step establishes clearance. Then a sample is admitted by closing valve V2, opening valve V1 and making such adjustments of probe P and line LI as may be necessary (if any) to assure sample acquisition. Jets J adjust and stabilize the new sample.

Temperature controls 134–138 and 142–146, described above, establish very coarse and less coarse thermal controls countering sample temperature variations.

An electronic signal processing apparatus baseline is established in 30–40 cycles (each having (+) and (−) sub-cycles with addition of (C+) and (C−) to detect an offset and compensate for it). Further adjustment is established by coils 124 to adjust H0 and this is enabled by ten to twenty field check cycles of FID curve generation. The (C−) FID is subtracted from the (C+) FID, i.e., the absolute C values are added to obtain a workable FID derivative—which has a maximum value at resonance. H0 is adjusted via coil current generator 117 and coils 124 until such maximum is achieved. These measurements are taken in a reliable region for such purpose, i.e., the expontial region of t3-t4 [the above baseline measurements are also taken there]. Adequate field adjustment is usually made in less than seven cycles.

Then fifty to five hundred cycles are conducted to obtain a useable measurement. Each of those fifty to five hundred cycles involves a modulated transmission/reception/flash A-D conversion, and storage of data. The curves are then averaged for curve fitting, to a t0 intercept and B0/A0+B0 ratio establishment. Similar cycles, but somewhat abbreviated can be applied for Quick FID, field check and baseline correction purposes. Each of the sub-cycles [(+) and (−)] of each such cycle involves a capture of thousands of FID points and utilization of hundreds of such points in data reduction.

Where multiple cycles are applied for a single measurement, the amplitudes of (digitized) curve C points are stored and a least squares fit to such data points is established. Further, plus and minus values are taken in alternation to eliminate zeroing errors as noted above.

The area under a square derivative of the desired exponential is integrated. The area under a squared derivative of the Gaussian (FID minus exponential) is also integrated. The square roots of the areas are taken and a ratio is established which is L/(KS+L) where L is liquid (moisture) value derived from the exponential, K a constant and S is the solid related quantity related to the Gaussian, KS+L being a measure of the total protons affected by resonance excitation (and capable of being so affected).

It has also been discovered as greater accuracy and reliability are obtained that sample tube composition can distort readings. If glass is not used (and it is preferred to avoid glass in industrial usage), then the replacement should not be a hydrocarbon plastic. But flurocarbons can be effective in several applications since signals from fluorine act out of resonance (with conditions tuned to resonance for hydrogen in moisture measurements) and can be distinguished from moisture related readings at the levels of sensitivity required for such readings and if desired can be filtered (or distinguished). In other cases of higher sensitivity measurements, e.g., for gauging relative proportions of amorphous and crystalline species in mixtures thereof, the sample container should be glass or non-protonic ceramic. In some instances, however, fluorocarbon or reinforced fluorocarbon can be used acceptably for plastics measurement. In all such cases the point is to avoid sample containers with species that can couple with transmitted energy and generate a FID decay curve mimicing the samples.

Figure 5:
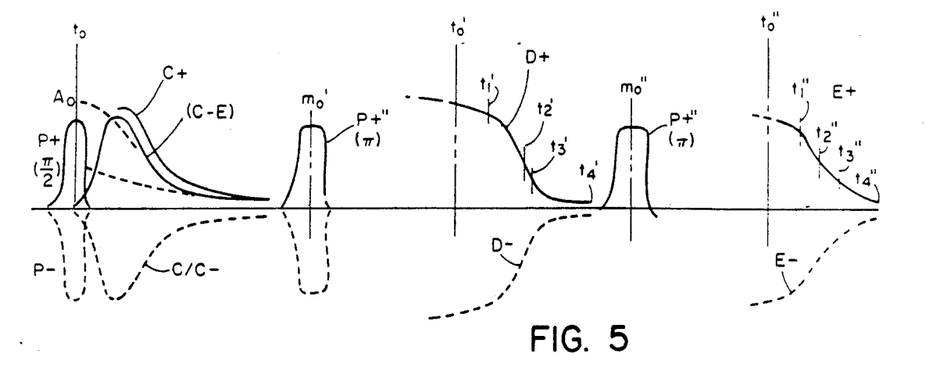
FIG. 5 is a voltage-time waveform for free induction decay (FID) of the embodiment of FIGS. 1-2 modified for Hahn spin echo utilization.

FIG. 5 shows another NMR decay waveform with repetition of terminology of identical components of the FIG. 3 NMR decay waveform discussed above. In a modification of operation of the FIG. 1-2 method and apparatus (and in modification of the structure and control settings thereof to effect such modified operation), each waveform is triggered by further pulses centered at mo' and mo" to cause Hahn spin echo responses to occur. The falling portions of the echoes (henceforth called D and E) have the same general patterns as the original FID C, excepting that D and E, particularly the latter are based primarily on response of the sample with nil response of non-fat solids and non-oil and non-solvent liquid components, whereas FID C is a measure of significant response to pulse excitation by all of solids, moisture and oil/fat or solvent components.

Times t1', t2', t3', t4' and t1", t2", t3", t4" are defined for D and E, respectively, as rough analogs of the t1, t2, t3, t4 points of FID C discussed above. However, there are significantly different effects in echoes (arising from 180° rotation) compared to C (arising from 90° rotation). FID C has a duration of about one millisecond order of magnitude and each of the echoes has a duration, typically of about two milliseconds order of magnitude as controlled by selective timing of P', P" in relation to P; but these intervals can be set as substantially more or less for different materials to be sampled and different sets of instrument electronics specification. Almost all the time of C is occupied in the decay process, compared to the latter half of each of the echoes. The effective beginning of decay for D and E is t0' and t0" at the actual peaks of these curves (whereas t0 for C is set at the middle of the excitation pulse. The decays +C/D/E are alternated with −C/D/E sub-cycles for the same purposes as +C/−C sub-cycles in FIG. 3, discussed above. The pulses P+/P− which initiate FID's C+/C− effect 90° (pi/2) rotation of protons while the pulses P+, P', P"+, P"− for +D, −D, +E, −E respectively effect 180° (pi) rotation.

Figure 6:
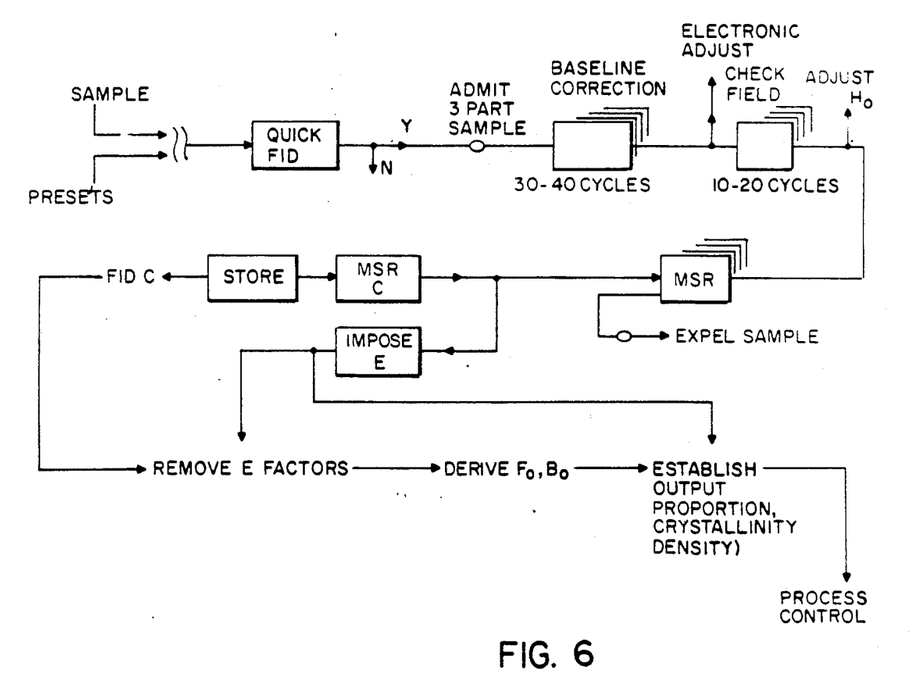
FIG. 6 is a flow chart of measuring steps utilizing the FIG. 1-2 embodiment, modified for Hahn spin echo utilization, including its signal processing elements (the activity of which is described by the FIG. 5 waveform) and also indicating density as well as moisture measurement.

The block diagram of operations of FIG. 6 for such a modified system includes the same artifacts as are described above in connection with FIG. 4, i.e. sample region clearance check by a Quick FID, multiple cycles of baseline correction and field checking (using simply P+, P− excitation) with consequent adjustments and then measurement substantively in accordance with the use of Hahn spin echo as described in connection with FIG. 5 above.

The signal processing of this measurement involves storage of digitized data points of the C and E decays, substraction of E from the C and then processing of an adjusted FID C essentially as described above in connection with FIGS. 3-4, with use of time-zero intercepts and/or integrals of Gaussian and exponential subsidiary curves derived from adjusted FID C. In some cases the peak of the E decay is used to quantify the solvent or oil/fat component(s).

Figure 7:
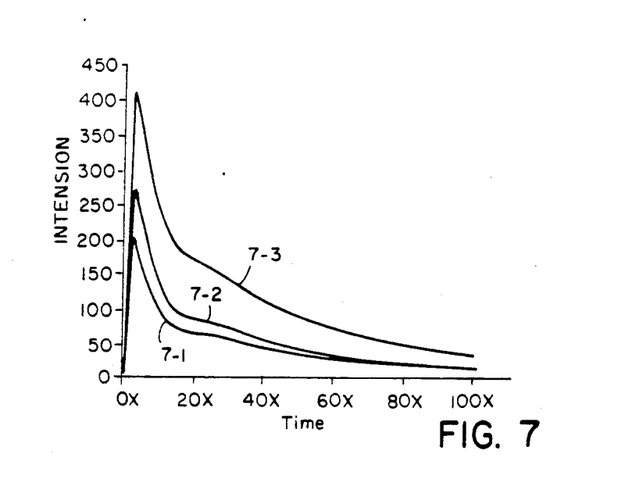
FIG. 7 is voltage (or other varied intensity parameter)-time trace for FID curves derived from samples of different densities using the above cited modified embodiment of the present invention affording relative and absolute density measurements of samples.

Additionally the data of FID C before or after adjustment by substraction of E is utilizable as a determinant of density on an absolute or relative basis. FIG. 7 shows FID's taken for polyethylene samples 7-1, 7-2, 7-3 of highest, less and least density. The curves are sufficiently distinct so that the differences are detectable by the signal processing means described above.

Figure 9A:
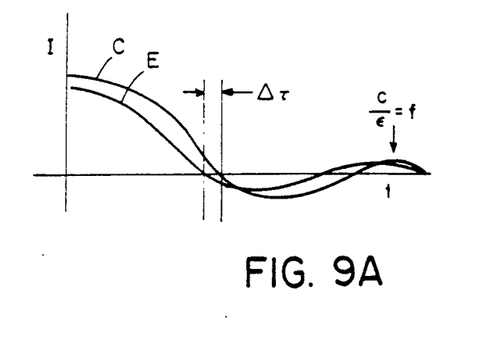
FIGS. 9A, 9B, 9C are intensity (I) vs. time (t) decay curves illustrating the operation of the modified embodiment according to further aspects thereof for establishing decay time constant shifts and scaling pre-set factors and for measuring a solvent or oil/fat or like further component of a sample by simple peak readings (averaged) instead of (reuse of) full FID analysis.
Figure 9B:
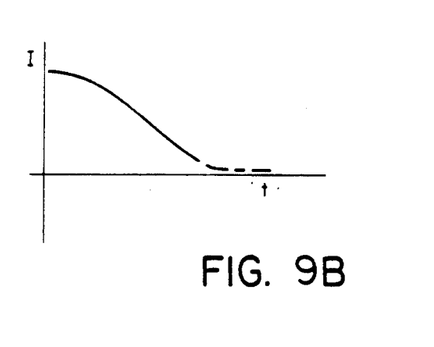
Figure 9C:
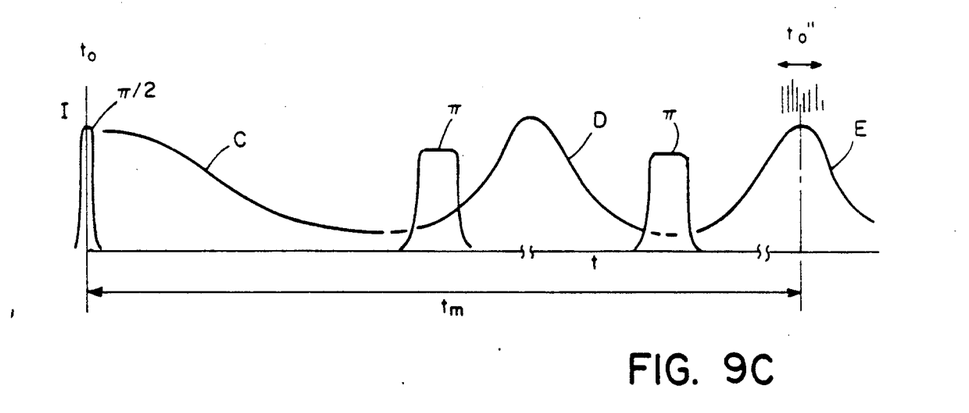

The appropriate t0" time setting of the E peak itself is determined as a presettable calibration factor for the instrument as applied to a certain type of material to be analyzed on-line over subsequent days (or weeks or months) of measurement. FIGS. 9A, 9B, 9C illustrate how this is done. FIG. 9A shows the C and E curves as developed by running the curves C, D, E of FIG. 5 with a roughly calculated t0" under non-resonance coupling conditions (deliberately induced at coil 100, FIGS. 1-2 as compared to a resonant decay curve shown e.g., in FIG. 9B) and superimposed. The difference of x-axis intercepts (Delta t, determined by shifting the curves until the zero crossings of C and E coincide) provides a correction factor to apply to the rough t0" to provide an adjusted t0"-a relative to t0 for use in later runs at resonance of FID decay with Hahn spin echo (FIG. 9C). That is, in such later runs the digitizer/flash converter (105-1, FIG. 1) is gated open at a time t0a" after the time t0. The last peaks (LP) of C and E in FIG. 9 are also analyzed to obtain a correction factor f, as the ratio C/E, to apply to later E readings to compensate for attenuation of t1 compared to what it would be if t0" coincided with t0 in reality, rather than as an arbitrary superimposition. This is a valid correction because C at LP is wholly due to solvent or oil/fact effects and the measured E is smaller than the measured C at LP only because of the attenuation.

Further, the intensity I parameter (e.g. voltage) is measured over a range including the nominal location of t0 and averaged to provide an average I usable with greater reliability.

Finally, due account must be taken of the relative quantity of protons (or other NMR-active species) per gram in each phase (e.g., solid, water, oil/fat) of interest. Appropriate calibration constants can be developed for determining concentrations of those phases or components or other percentages data, e.g. crystallinity, in a mixture. For example, the proportion P of, say, oil/fat is determined by:

$$P = \frac{K_e E_o}{K_e E_o + K_a A_o + K_b B_o}$$

where $K_e, K_a, K_b$ are calibration factors derived from standard materials and $A_o, B_o, E_o$ are the t0 intercepts after application of the above correction factors. Density (d) of a sample material as a whole can be determined either through curve analysis discussed above in connection with FIGS. 7-1, 7-2, 7-3 or for plastics (and other materials) throught the equation:

$$d = \frac{M[KaAo]}{[KaAo + KbBo + KeEo]} + N$$

where the bracketed fraction is the crystallinity proportion and M and N are empirically derived calibration factors (usually constants for the materials, consistently applied after initial determination). Densities of the components would normally be additional terms in the equation; but for plastics the crystalline and amorphous components have closely related fundamental densities and density terms can drop out (except insofar as built into the M, N factors).

For other materials the equation would be:

$$d = \frac{(M)[KAoda]}{[KAoda + KBodb + KEode]} + N$$

where da, db and de are component densities.

Figure 8:
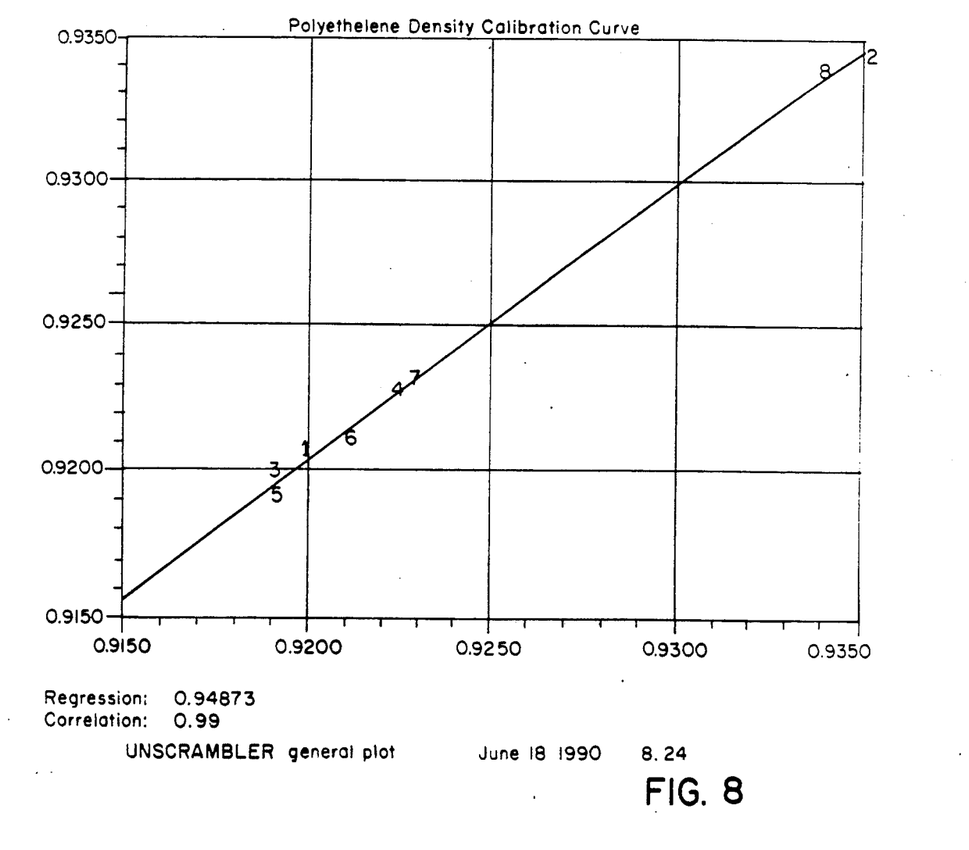
FIG. 8 is a calibration curve for absolute density measurement using the above cited embodiments of the present invention as applied to polyethylene.

FIG. 8 shows a calibration curve of such polyethylene density measurements by the present invention (y axis) vs. standard method (e.g. oil bath flotation) density measurements (x axis), illustrating the efficacy of the present invention. Other standard methods include acoustic transmissivity.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. In a nuclear magnetic resonance system for industrial process monitoring comprising:
   (a) means for accessing successive samples from an industrial process, placing them in a sample measuring region and discarding successive such samples from said sample measuring region,
   (b) means for applying a base magnetic field to the sample measuring region to effect precession of sample nuclei and for applying a resonant excitation pulse to the sample measuring region to modify the precession and means defining receive antenna coil means and signal translating means interacting with a sample in said region to detect relaxation of the sample at the coil means as a free induction decay signal which is measurable as a free induction decay curve via said signal translating means,
   (c) means for digitizing the free induction decay curve and automatically analyzing the digitized curve to zero axis intercepts of Gaussian and exponential components of the decay curve and extracting a ratio of the intercept of one of said components to the sum of intercepts of said components,
   the improvement comprising the provision therein of means for extending each of the said decay curves established in multiple repetitions of the said curve establishment and automatic analysis sequence by Hahn spin-echo re-focus/decay to capture data related to a further sub-component(s) of the sample for enhancing the accuracy of the ratio determination of (c) above and/or to identify proportion of the further sub-component(s).

2. System in accordance with claim 1 wherein two pi refocus pulses are applied for generation of the Hahn spin echoes.

3. System in accordance with claim 1 and further comprising means for determining a time window for gating spin echo detection at a correct zero-axis intercept relatable to an original intercept of the free induction decay curve.

4. System in accordance with claim 3 and further comprising means to effect such time window determination and also to compensate for attenuation of the spin echo response relative to initial response of the free induction decay by off-resonance comparison.

5. System in accordance with claim 1 constructed and arranged to provide proportionality.

6. System in accordance with claim 1 constructed and arranged to provide crystallinity output.

7. System in accordance with claim 1 constructed and arranged to provide moisture output.

8. System in accordance with claim 1 constructed and arranged to provide density output.

* * * * *